United States Patent
Rousseau et al.

(10) Patent No.: US 10,338,032 B2
(45) Date of Patent: Jul. 2, 2019

(54) AUTOMATED QUALITY DETERMINATION OF JOINTS

(71) Applicant: GM GLOBAL TECHNOLOGY OPERATIONS LLC, Detroit, MI (US)

(72) Inventors: Ingrid A. Rousseau, Clawson, MI (US); Selina X. Zhao, Rochester Hills, MI (US); Hamid G. Kia, Bloomfield Hills, MI (US)

(73) Assignee: GM Global Technology Operations LLC., Detroit, MI (US)

( * ) Notice: Subject to any disclaimer, the term of this patent is extended or adjusted under 35 U.S.C. 154(b) by 382 days.

(21) Appl. No.: 15/358,301

(22) Filed: Nov. 22, 2016

(65) Prior Publication Data

US 2018/0143164 A1    May 24, 2018

(51) Int. Cl.
*G01N 29/06* (2006.01)
*G01N 29/44* (2006.01)

(52) U.S. Cl.
CPC ....... *G01N 29/069* (2013.01); *G01N 29/4481* (2013.01); *G01N 2291/0289* (2013.01); *G01N 2291/267* (2013.01)

(58) Field of Classification Search
CPC .......................... G01N 29/069; G01N 29/4481
See application file for complete search history.

(56) References Cited

U.S. PATENT DOCUMENTS

| | | |
|---|---|---|
| RE35,423 E | 1/1997 | Adams et al. |
| 6,404,206 B1 | 6/2002 | Sperschneider |
| 2002/0040922 A1 | 4/2002 | Kobayashi |
| 2005/0005700 A1 | 1/2005 | Abbasi et al. |
| 2009/0034828 A1* | 2/2009 | Ferro .................. G01N 29/0645 382/144 |
| 2011/0162184 A1 | 7/2011 | Zdravkovic et al. |

(Continued)

FOREIGN PATENT DOCUMENTS

| | | |
|---|---|---|
| WO | 2006057836 A2 | 6/2006 |
| WO | 2016038395 A1 | 3/2016 |

OTHER PUBLICATIONS

Yang Ou and Li Yueping; "Quality Evaluation and Automatic Classification in Resistance Spot Welding by Analyzing the Weld Image on Metal Bands by Computer Vision"; International Journal of Signal Processing, Image Jrocessing and Pattern Recognition, vol. 8, No. 5 (2015), pp. 301-314.

*Primary Examiner* — David Z Huang
(74) *Attorney, Agent, or Firm* — Quinn IP Law (57) ABSTRACT

An assembly includes a sensor configured to obtain a data scan of a joint. A controller is operatively connected to the sensor. The controller includes a processor and tangible, non-transitory memory on which is recorded instructions for executing a method for automated quality assessment of the joint. Execution of the instructions by the processor causes the controller to: obtain the data scan of the joint (via the sensor) and generate a first image based on the data scan. The first image is divided into a plurality of pixels having respective numeric values. The controller is programmed to identify a region of interest as the plurality of pixels from the first image with a respective numeric value greater than a threshold value ($I_0$). The controller is programmed to assess joint quality based on a porosity factor (PF) determined at least partially from the data scan.

20 Claims, 3 Drawing Sheets

(56) References Cited

U.S. PATENT DOCUMENTS

2014/0216158 A1* 8/2014 Sanabria Martin .. G01N 29/069
 73/588
2015/0253288 A1 9/2015 Spencer et al.

* cited by examiner

AUTOMATED QUALITY DETERMINATION OF JOINTS

INTRODUCTION

The present disclosure relates generally to automated quality determination of joints. The quality of a joint may be assessed based on many different factors. The quality assessment of joints is generally done through manual testing of joints. However, this is dependent on operator skills and may be time-consuming. Additionally, some joints may be difficult to assess through visual inspection, such as for example, joints obtained from ultrasonically welding or adhesively bonding substrates such as polymers, metals, composites and other materials.

SUMMARY

An assembly includes a sensor configured to obtain a data scan of a joint. A controller is operatively connected to the sensor. The controller includes a processor and tangible, non-transitory memory on which is recorded instructions for executing a method for automated quality assessment of the joint. The method allows for an automated determination of joint quality, with greater accuracy and speed. It is applicable to multiple joint types and materials. The method enables the development, testing and implementation of new materials and associated joining techniques.

Execution of the instructions by the processor causes the controller to: obtain the data scan of the joint (via the sensor) and generate a first image based at least partially on the data scan. The first image is divided into a plurality of pixels having respective numeric values. The controller is programmed to identify a region of interest as the plurality of pixels with the respective numeric value greater than a threshold intensity ($I_0$). The sensor may include a transmitter configured to transmit ultrasonic waves into the joint and a receiver configured to receive the ultrasonic waves reflected through the joint.

Prior to obtaining the data scan, the controller may be programmed to determine if one or more entry conditions are satisfied. If each of the one or more entry conditions are satisfied, the controller is programmed to select one of a predefined set of joint categories. The predefined set of joint categories each defines a respective minimum joint area ($A_{min}$). The sensor includes a probe exerting a pressure on a surface overlying the joint. Prior to obtaining the data scan, the controller may be programmed to determine if a position of the probe relative to the surface is within a predefined position range, and if the pressure applied by the probe is within a predefined pressure range. The probe may be positioned at an angle relative to the surface overlying the joint. The controller may be programmed to determine whether the angle may be within a predefined angle (tolerance) range, prior to obtaining the data scan.

The sensor includes a transmitter configured to transmit multiple signals into the joint and a receiver configured to receive the multiple signals reflected through the joint. A recorder is configured to record a respective travel time for the multiple signals to arrive at the plurality of pixels. The controller is programmed to obtain the respective travel time for each of the plurality of pixels in the region of interest, via the recorder. A first area (A) is obtained as a total area of the plurality of pixels in the region of interest having the respective travel time within a predefined time range.

The controller is programmed to determine if the first area (A) is at or above the respective minimum joint area ($A_{min}$). If the first area (A) is at or above the respective minimum joint area ($A_{min}$), an exterior boundary is generated. The generation of the exterior boundary may include: identifying one or more edge pixels from the plurality of pixels and connecting each of the one or more edge pixels to generate one or more borders. Each of the edge pixels are directly adjacent to eight respective neighboring pixels. The edge pixels may be defined such that at least one of the eight respective neighboring pixels has a respective numeric value greater than the intensity threshold ($I_0$) (or travel time within the predefined time range or both) and at least another of the eight respective neighboring pixels N1, to N8, has a respective numeric value less than the intensity threshold ($I_0$) (or travel time outside the predefined time range or both). A largest of the one or more borders is selected as the exterior boundary.

The controller is programmed to obtain a second area (B) as a total area of the plurality of pixels inside the exterior boundary. A porosity factor (PF) is determined based in part on the first area (A) and the second area (B) such that $PF=[1-(A/B)]$. If the porosity factor (PF) is at or below a threshold porosity factor ($PF_0$), the joint is categorized as acceptable. If the porosity factor (PF) is above the threshold porosity factor ($PF_0$), the joint is flagged for further evaluation, which may include repairs or disqualification.

The above features and advantages and other features and advantages of the present disclosure are readily apparent from the following detailed description of the best modes for carrying out the disclosure when taken in connection with the accompanying drawings.

DETAILED DESCRIPTION

Figure 1:
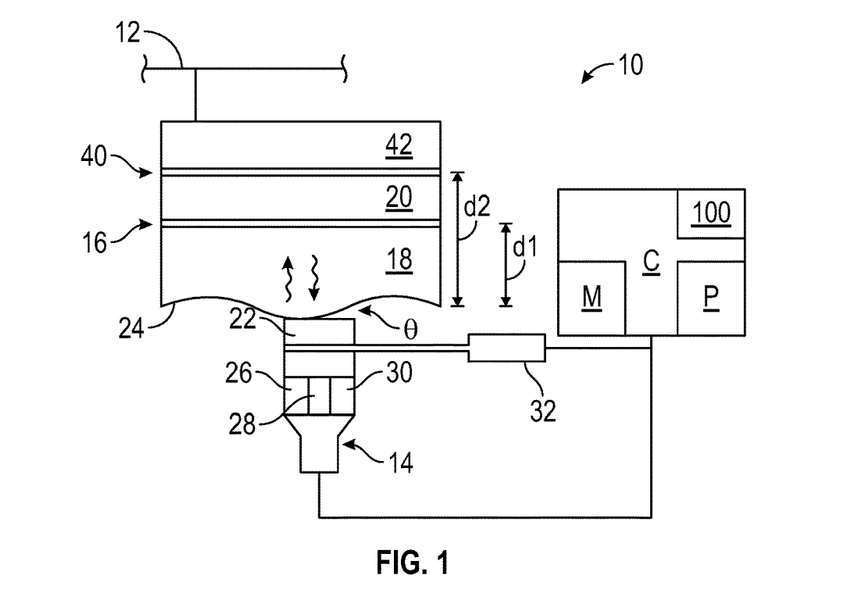
FIG. 1 is a schematic illustration of an assembly for automated quality determination of a joint, the assembly having a sensor and a controller.

Referring to the drawings, wherein like reference numbers refer to like components, FIG. 1 schematically illustrates an assembly 10, which may be part of a device 12. The device 12 may be a mobile platform, such as, but not limited to, a standard passenger car, sport utility vehicle, light truck, heavy duty vehicle, ATV, minivan, bus, transit vehicle, bicycle, robot, farm implement, sports-related equipment, boat, plane, train. The device 12 may be a non-mobile platform, such as, but not limited to, construction equipment, consumer goods and toys. The device 12 may take many different forms and include multiple and/or alternate components and facilities.

Referring to FIG. 1, the assembly 10 includes a sensor 14 configured to obtain a data scan of a joint 16 formed between a first member 18 and a second member 20. The joint 16 may be formed, for example, by ultrasonically welding the first member 18 and the second member 20. The joint 16 may formed by bonding the first member 18 and the second member 20 with an adhesive. The joint 16 may be formed by fusing or attaching the first member 18 to the second member 20 via methods employed by those skilled in the art. Depending on the type of substrate employed and the end applications, the methods include infra-red heating, hot plate, joule heating, spot welding, etc. The first member 18 and second member 20 may be composed of various materials employed by those skilled in the art, including but not limited to, amorphous materials, semi-crystalline materials, metals, polymers and (polymer) composites. The first member 18 and second member 20 may be composed of steel, aluminum, magnesium, thermosets or thermoplastics polymers based on acrylate, Acrylonitrile Butadiene Styrene (ABS), Acrylonitrile Styrene Acrylate (ASA), Polycarbonate (PC) or Polypropylene (PP) chemistries or others that will be evident to those skilled in the art. These may be further reinforced with various materials such as glass fibers, carbon fibers and clays or contain additives suitable for the end up application and/or manufacturing process, such as UV stabilizers, temperature stabilizers, dyes or pigments, internal mold release agents, and the like, or a combination thereof.

Referring to FIG. 1, the sensor 14 includes a probe 22 that is placed over a surface 24 overlying the joint 16. The sensor 14 includes a transmitter 26 configured to emit a plurality of identical signals into the joint 16 at the surface 24 in order to cover a desired geometrical area that can be a discrete point, a line, square or a round-shaped area. In one example, the signal is a phased-array ultrasonic wave. The ultrasonic wave is reflected by voids in the joint 16 and conducted or propagated by areas that are welded, bonded or otherwise fused. The reflected waves arise from an air/material interface or an interface between the first member 18 and second member 20. The reflected waves arise from any interface with a significant change in intrinsic sound attenuation properties, such as air/material interface or an interface between a material A and a material B (where the first member 18 and second member 20 are composed of materials A, B, respectively) provided that material A and material B possess different sound attenuation properties. A receiver 28 is configured to receive the signals reflected back after travelling through the joint 16. A recorder 30 is configured to record the time taken for the signal to return after being transmitted.

Figure 2:
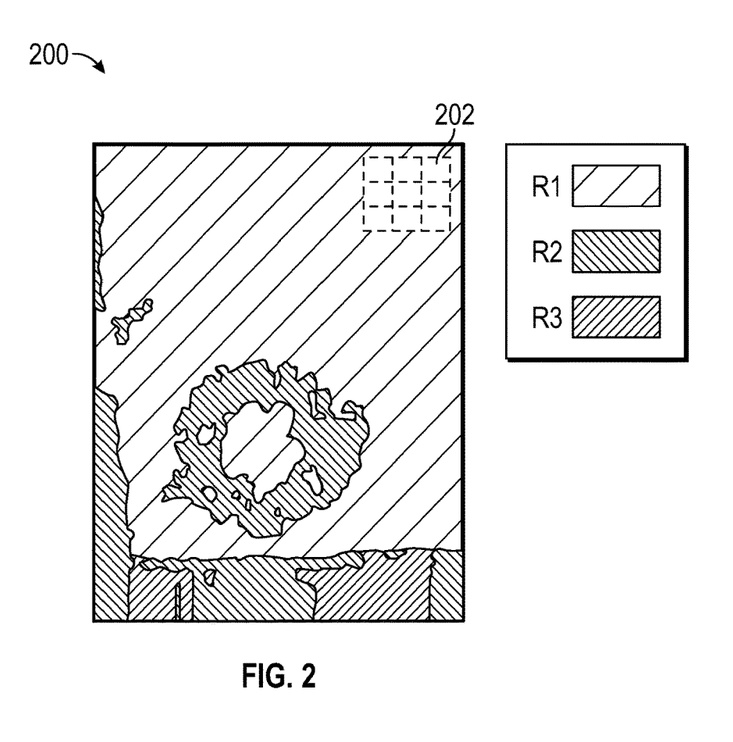
FIG. 2 is a schematic illustration of a first image obtained by the sensor of FIG. 1.

Referring to FIG. 1, a controller C is operatively connected to the sensor 14. The controller C is programmed to generate a first image of the joint 16, based at least partially on the data scan obtained via the sensor 14. An example of a first image 200 of the joint 16 is shown in FIG. 2. The probe 22 may be configured to slide or otherwise translate in an X-Y plane along the surface 24 and obtain multiple images that are combined to form the first image 200. The controller C includes at least one processor P and at least one memory M (or non-transitory, tangible computer readable storage medium) on which are recorded instructions for executing method 100 for automated quality assessment of the joint, described in detail in FIG. 3. The memory M can store controller-executable instruction sets, and the processor P can execute the controller-executable instruction sets stored in the memory M.

Figure 3:
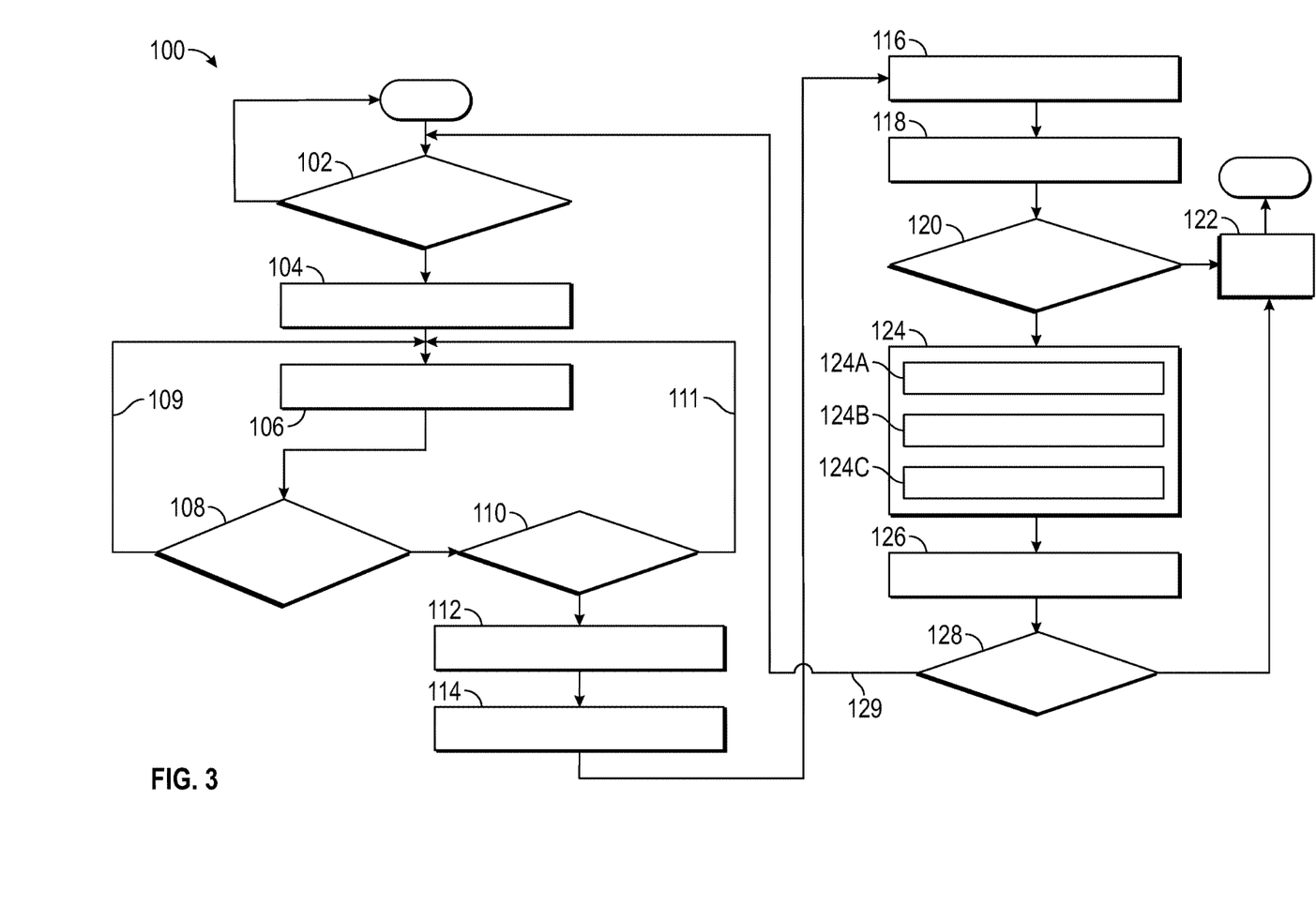
FIG. 3 is a schematic flow diagram for a method executable by the controller of FIG. 1.

Referring now to FIG. 3, a flowchart of the method 100 stored on and executable by the controller C of FIG. 1 is shown. Method 100 need not be applied in the specific order recited herein. Furthermore, it is to be understood that some blocks may be eliminated. The controller C of FIG. 1 is specifically programmed to execute the blocks of the method 100. The start and end of the method 100 are shown by "S" and "E," respectively.

Referring to FIG. 3, the method 100 may begin with block 102, where the controller C is programmed or configured to determine if one or more entry conditions are satisfied. The entry conditions include placing the sensor 14 on a test or "check" joint having measured or identified properties. The image is collected on the check joint. The image is then compared to a look-up table having respective threshold values. If the instrument parameters are within respective threshold values, the instruments (i.e., controller C, processor P, sensor 14, etc.) are deemed to be functioning properly and the method 100 proceeds to block 104.

In block 104, the controller C is programmed to select one of a predefined set of joint categories, based in part on the properties of the joint 16. The predefined parameters may depend on the type of joint, the material that the first and second members 18, 20 are made of, the size and thickness of the joint 16, and the number of layers in the joint 16. The predefined parameters may be stored in a look-up table or data repository. Sets of joint properties may be obtained from a series of laboratory measurements using selected material types, number of layers, dimensions, joining techniques, stack-up depth, strength values, etc. These relate to input parameters for a selected joint type to be analyzed, such as for example, sound attenuation, inspection tool frequency, inspection tool pulse rate, etc. Each of the predefined set of joint categories defines a respective minimum joint area ($A_{min}$). The predefined set of joint categories may define a respective minimum joint diameter ($D_{min}$).

In block 106, the controller C is programmed to place the sensor 14 on the surface 24 overlying the joint 16 (see FIG. 1). The probe 22 (of the sensor 14) may be positioned via a robotic arm 32 controllable by the controller C. Alternatively, the controller C may direct a user to manually position the probe 22 via a message displayed on a user interface.

The method 100 proceeds to block 108, where the controller C is programmed to determine if the position of the sensor 14 (e.g., distance from the joint 16) is within a predefined position range and determine if the pressure applied by the probe 22 is within a predefined pressure range. If the position and pressure are within the respective predefined ranges, the method 100 proceeds to block 110. If not, the method 100 proceeds to block 106 (as indicated by line 109) for a re-alignment of the probe 22 relative to the joint 16.

In block 110, the controller C is programmed to determine if the angle θ of the probe 22 relative to the surface 24 is within a predefined angle range (tolerance). If it is, the method 100 proceeds to block 112. If not, the method 100 proceeds to block 106 (as indicated by line 111) for a re-alignment of the probe 22 relative to the joint 16. The predefined position, pressure and angle ranges may be obtained in a series of laboratory measurements.

In block 112, the controller C is programmed to obtain the data scan of the joint 16 (via the sensor 14) and generate a first image 200 (see example shown in FIG. 2) based at least partially on the data scan. The first image 200 is divided into a plurality of pixels 202, each having respective numeric values reflecting the amplitude of the signal received by the sensor 14.

Referring to the legend in FIG. 2, the first image 200 is divided into first, second and third regions R1, R2 and R3, respectively. The first region R1 represents pixels 202 with respective numeric values that are above a threshold value ($I_0$), e.g. 10,000 units for example. The second region R2 represents pixels 202 with respective numeric values that are at or below the threshold value ($I_0$). The third region R3 represents pixels 202 with respective numeric values that are zero or almost zero. In one example, the third region R3 represents pixels that are less than 0.1% of the threshold value ($I_0$).

In block 114, the controller C is programmed to identify a region of interest as the plurality of pixels 202 with the respective numeric value lower than a threshold intensity ($I_0$). Referring to FIG. 2, the region of interest here is the combination of the second and third regions (R2+R3). The method 100 proceeds to block 116, where the controller C is programmed to obtain a respective travel time for the respective signal received at each pixel 202, from the time each signal was initially emitted by the probe 22, in the second and third regions R2 and R3 of FIG. 2. The controller C is programmed to identify pixels 202 with a respective travel time outside a predefined time range, i.e., ($t_0$-$t_1$). This enables the elimination of data from other joints (such as secondary joint 40 formed between the second member 20 and a third member 42, see FIG. 1), material defects such as gaseous or fluid voids, end of parts or other material discontinuities, and other artifacts, and therefore, isolation of data emanating from the joint of interest (the joint 16 in this case). The travel time incorporates the time taken for the signal to reach a certain depth (depth d1 for the joint 16 and depth d2 for the secondary joint 40) and travel back. Other methods to measure the time that it takes for the signal to arrive from the joint 16 may be employed.

Figure 4:
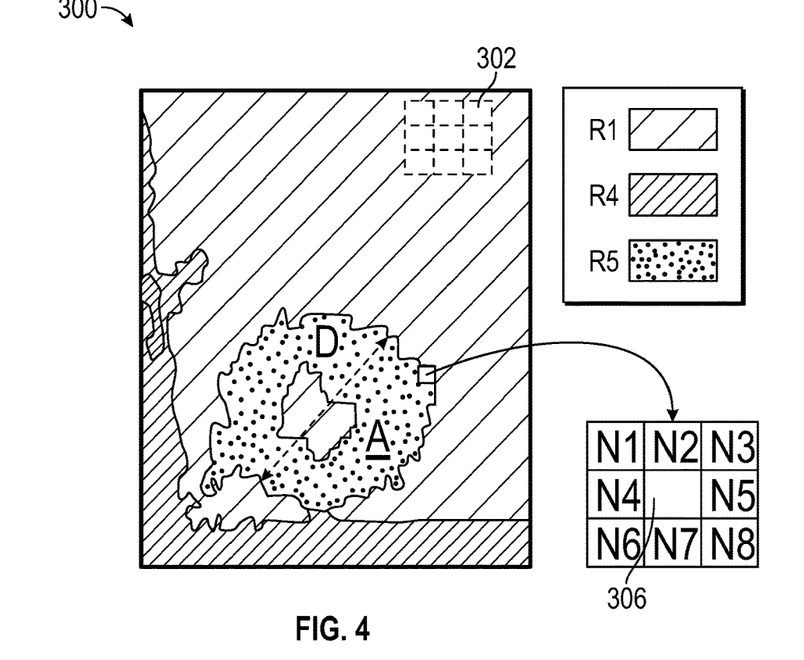
FIG. 4 is a schematic illustration of a second image obtained from the first image, after partial execution of the method of FIG. 3.

Referring to FIG. 4, a second image 300 is shown, based in part on the first image 200. Referring to FIG. 4, the region of interest is divided into a fourth region R4 and a fifth region R5. The fourth region R4 includes pixels 302 with a respective travel time within a predefined time range, i.e., ($t_0$-$t_1$). The fourth region R4 includes pixels 302 with a respective travel time outside the predefined time range. The method 100 proceeds to block 118, where the controller C is programmed to obtain a first area A, as a total area of the pixels 302 in the fifth region R5.

The method 100 proceeds to block 120, where the controller C is programmed to determine if the first area A is at or above the minimum joint area ($A_{min}$) obtained in block 104. If the first area A is below the minimum joint area ($A_{min}$), the method 100 proceeds to block 122. In block 122, the controller C is programmed to flag the joint 16 to an operator for further evaluation, for example, by displaying a message on a user interface. The further evaluation may include repairs to the joint 16 or disqualification. If the first area A is at or above the respective minimum joint area ($A_{min}$), the method 100 proceeds to block 124. Additionally, in block 120, the controller C may be programmed to determine a first diameter D (shown in FIG. 4) of the pixels 302 in the fifth region R5, and determine if the first diameter D is at or above a minimum joint diameter ($D_{min}$) (obtained in block 104). If the first diameter D is below the minimum joint diameter ($D_{min}$), the method 100 proceeds to block 122, where the joint 16 is flagged for further evaluation.

Figure 5:
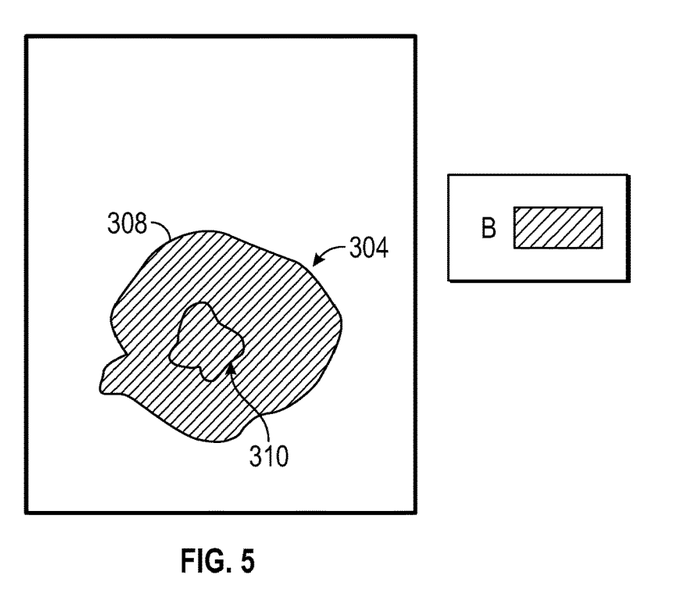
FIG. 5 is a schematic illustration of an exterior boundary obtained from the second image of FIG. 4.

In block 124, the controller C is programmed to generate an exterior boundary 304 for the pixels 302 in the region of interest having the respective travel time within the predefined time range, i.e., the pixels 302 in the fifth region R5. FIG. 5 is a schematic illustration of the exterior boundary 304 obtained from the second image 200 of FIG. 4. Block 124 includes the sub-blocks 124A, 124B and 124C.

In sub-block 124A, the controller C is programmed to identify one or more edge pixels 306 from the pixels 302 in the fifth region R5. Referring to FIG. 4, each edge pixel 306 is directly adjacent to eight respective neighboring pixels, N1 to N8. In one example, an edge pixel 306 may be defined such that at least one of the eight respective neighboring pixels, N1 to N8, has a respective numeric value greater than the intensity threshold ($I_0$) (or travel time within the predefined time range or both) and at least another of the eight respective neighboring pixels N1, to N8, has a respective numeric value less than the intensity threshold ($I_0$) (or travel time outside the predefined time range or both). In another example, the edge pixels 306 may be defined such at least two of the eight respective neighboring pixels, N1 to N8, have a respective numeric value greater than the intensity threshold ($I_0$) and at least another two of the eight respective neighboring pixels N1, to N8, have a respective numeric value less than the intensity threshold ($I_0$).

In sub-block 124B, the controller C is programmed to connect the centers (or corners) of the neighboring edge pixels 306 to create one or more borders, such as first border 308 and second border 310 of FIG. 5. Only the edge pixels 306 that are neighboring or adjacent are connected, in order to avoid inadvertently connecting the first border 308 to the second border 310.

In sub-block 124C, the controller C is programmed to select the exterior boundary 304 as the largest (in perimeter) one of the one or more borders. Here, as the first border 308 is larger than the second border 310. The method 100 proceeds to block 126 from block 124.

In block 126, the controller C is programmed to obtain a second area B as a total area of pixels 302 inside the exterior boundary 304. The second area B is shown in the legend of FIG. 5. The first and second areas A and B may be determined in terms of the number of pixels or in physical dimensions such as, for example, millimeter squared ($mm^2$).

In block 128, the controller C is programmed to determine a porosity factor (PF) based in part on the first area A and the second area B such that:

$$PF=[1-(A/B)].$$

If the porosity factor (PF) is above a threshold porosity ($PF_0$), the method 100 proceeds to block 122. In block 122, the controller C is programmed to flag the joint 16 for further evaluation (and possible repair) or disqualification. In one example, the threshold porosity ($PF_0$) is 0.2. If the porosity factor (PF) is at or below the threshold porosity ($PF_0$), the joint quality is deemed as acceptable and the method 100 loops back to block 102, as indicated by line 129, to assess the quality of the next joint (if applicable). The controller C of FIG. 1 may be an integral portion of, or a separate module operatively connected to, other controllers of the device 12. The controller C includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above, and may be accessed via a network in one or more of a variety of manners. A file system may be accessible from a computer operating system, and may include files stored in various formats. An RDBMS may employ the Structured Query Language (SQL) in addition to a language for creating, storing, editing, and executing stored procedures, such as the PL/SQL language mentioned above.

The detailed description and the drawings or figures are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. An assembly comprising:
    a sensor configured to obtain a data scan of a joint, the sensor including a probe exerting a pressure on a surface overlying the joint;
    a controller operatively connected to the sensor, the controller including a processor and tangible, non-transitory memory on which is recorded instructions for executing a method for automated quality assessment of the joint;
    wherein execution of the instructions by the processor causes the controller to:
        obtain the data scan of the joint, via the sensor;
        generate a first image based at least partially on the data scan, the first image being divided into a plurality of pixels having respective numeric values; and
        identify a region of interest as the plurality of pixels with the respective numeric value greater than a threshold intensity ($I_0$); and
    wherein the controller is programmed to, prior to obtaining the data scan:
        determine if one or more entry conditions are satisfied;
        if each of the one or more entry conditions are satisfied, select one of a predefined set of joint categories, the predefined set of joint categories each defining a respective minimum joint area ($A_{min}$);
        determine if a position of the probe relative to the surface is within a predefined position range; and
        determine if the pressure applied by the probe is within a predefined pressure range.

2. The assembly of claim 1, wherein:
    the sensor includes a transmitter configured to transmit ultrasonic waves into the joint; and
    the sensor includes a receiver configured to receive the ultrasonic waves reflected through the joint.

3. The assembly of claim 1, wherein:
    the sensor includes a probe positioned at an angle relative to a surface overlying the joint;
    wherein the controller is programmed to determine whether the angle is within a predefined angle range, prior to obtaining the data scan.

4. The assembly of claim 1, wherein:
    the sensor includes a transmitter configured to transmit multiple signals into the joint;
    the sensor includes a receiver configured to receive the multiple signals reflected through the joint; and
    the sensor includes a recorder configured to record a respective travel time for the multiple signals to arrive at the plurality of pixels; and
    the controller is programmed to:
        obtain the respective travel time for each of the plurality of pixels in the region of interest, via the recorder; and
        obtain a first area (A) as a total area of the plurality of pixels in the region of interest having the respective travel time within a predefined time range.

5. The assembly of claim 4, wherein the controller is programmed to:
    determine if the first area (A) is at or above the respective minimum joint area ($A_{min}$);
    if the first area (A) is at or above the respective minimum joint area ($A_{min}$), generate an exterior boundary of the plurality of pixels in the region of interest having the respective travel time within the predefined time range.

6. The assembly of claim 5, wherein the generation of the exterior boundary includes:
    identifying one or more edge pixels from the plurality of pixels;
    connecting each of the one or more edge pixels to generate one or more borders; and
    selecting a largest one of the one or more borders as the exterior boundary.

7. The assembly of claim 6, wherein:
    each of the one or more edge pixels are directly adjacent to eight respective neighboring pixels; and
    wherein the one or more edge pixels are defined such that at least one of the eight respective neighboring pixels has a respective numeric value greater than the intensity threshold ($I_0$) and at least another of the eight respective neighboring pixels N1, to N8, has a respective numeric value less than the intensity threshold ($I_0$).

8. The assembly of claim 6, wherein the controller is programmed to:
    obtain a second area (B) as a total area of the plurality of pixels inside the exterior boundary;
    determine a porosity factor (PF) based in part on the first area (A) and the second area (B) such that $PF=[1-(A/B)]$;
    if the porosity factor (PF) is at or below a threshold porosity factor ($PF_0$), categorize the joint as acceptable; and
    if the porosity factor (PF) is above the threshold porosity factor ($PF_0$), flag the joint for further evaluation.

9. A method for automated quality assessment of a joint in an assembly having a sensor and a controller, the method comprising:
    obtaining a data scan of the joint, via the sensor;
    generating a first image based at least partially on the data scan, via the controller, the first image being divided into a plurality of pixels having respective numeric values;
    identifying a region of interest as the plurality of pixels with the respective numeric value greater than a threshold intensity ($I_0$);
    transmitting multiple signals into the joint, via a transmitter in the sensor;
    receiving the multiple signals reflected through the joint, via a receiver in the sensor;
    recording a respective travel time for the multiple signals to arrive at each of the plurality of pixels in the region of interest, via a recorder in the sensor; and
    obtaining a first area (A) as a total area of the plurality of pixels in the region of interest having the respective travel time within a predefined time range.

10. The method of claim 9, further comprising:
    prior to obtaining the data scan, determining if one or more entry conditions are satisfied;
    if each of the one or more entry conditions are satisfied, selecting one of a predefined set of joint categories; and
    wherein the predefined set of joint categories each define a respective minimum joint area ($A_{min}$).

11. The method of claim 10, further comprising:
    determining if the first area (A) is at or above the respective minimum joint area ($A_{min}$);
    if the first area (A) is at or above the respective minimum joint area ($A_{min}$), generating an exterior boundary of the plurality of pixels in the region of interest having the respective travel time within the predefined time range;
    obtaining a second area (B) as a total area of the plurality of pixels inside the exterior boundary;
    determining a porosity factor (PF) based in part on the first area (A) and the second area (B) such that PF=[1−(A/B)];
    if the porosity factor (PF) is at or below a threshold porosity factor ($PF_0$), categorizing the joint as acceptable;
    if the porosity factor (PF) is above the threshold porosity factor ($PF_0$), flag the joint for further evaluation.

12. The method of claim 11, wherein the generation of the exterior boundary includes:
    identifying one or more edge pixels from the plurality of pixels;
    connecting each of the one or more edge pixels to generate one or more borders; and
    selecting a largest one of the one or more borders as the exterior boundary.

13. The method of claim 12, wherein:
    each of the one or more edge pixels are directly adjacent to eight respective neighboring pixels; and
    wherein the one or more edge pixels are defined such that at least one of the eight respective neighboring pixels has a respective numeric value greater than the intensity threshold ($I_0$) and at least another of the eight respective neighboring pixels N1, to N8, has a respective numeric value less than the intensity threshold ($I_0$).

14. The method of claim 9, wherein the sensor includes a probe exerting a pressure on a surface overlying the joint, further comprising:
    prior to obtaining the data scan, determining if a position of the probe relative to the surface is within a predefined position range; and
    determining if the pressure applied by the probe is within a predefined pressure range.

15. The method of claim 9, wherein:
    the sensor includes a probe positioned at an angle relative to a surface overlying the joint;
    wherein the controller is programmed to determine whether the angle is within a predefined angle range, prior to obtaining the data scan.

16. An assembly comprising:
    a sensor configured to obtain a data scan of a joint;
    a controller operatively connected to the sensor, the controller including a processor and tangible, non-transitory memory on which is recorded instructions for executing a method for automated quality assessment of the joint;
    wherein the sensor includes a transmitter configured to transmit multiple signals into the joint and a receiver configured to receive the multiple signals reflected through the joint;
    wherein execution of the instructions by the processor causes the controller to:
        obtain the data scan of the joint, via the sensor;
        generate a first image based at least partially on the data scan, the first image being divided into a plurality of pixels having respective numeric values;
        identify a region of interest as the plurality of pixels with the respective numeric value greater than a threshold intensity ($I_0$); and
    wherein the sensor includes a recorder configured to record a respective travel time for the multiple signals to arrive at the plurality of pixels, the controller being further programmed to:
        obtain the respective travel time for each of the plurality of pixels in the region of interest, via the recorder; and
        obtain a first area (A) as a total area of the plurality of pixels in the region of interest having the respective travel time within a predefined time range.

17. The assembly of claim 16, wherein the controller is programmed to, prior to obtaining the data scan:
    determine if one or more entry conditions are satisfied;
    if each of the one or more entry conditions are satisfied, select one of a predefined set of joint categories, the predefined set of joint categories each defining a respective minimum joint area ($A_{min}$).

18. The assembly of claim 17, wherein the controller is programmed to:
    determine if the first area (A) is at or above the respective minimum joint area ($A_{min}$);
    if the first area (A) is at or above the respective minimum joint area ($A_{min}$), generate an exterior boundary of the plurality of pixels in the region of interest having the respective travel time within the predefined time range;
    obtain a second area (B) as a total area of the plurality of pixels inside the exterior boundary;
    determine a porosity factor (PF) based in part on the first area (A) and the second area (B) such that PF=[1−(A/B)];
    if the porosity factor (PF) is at or below a threshold porosity factor ($PF_0$), categorize the joint as acceptable; and
    if the porosity factor (PF) is above the threshold porosity factor ($PF_0$), flag the joint for further evaluation.

19. The assembly of claim 17, wherein the generation of the exterior boundary includes:
- identifying one or more edge pixels from the plurality of pixels;
- connecting each of the one or more edge pixels to generate one or more borders; and
- selecting a largest one of the one or more borders as the exterior boundary.

20. The assembly of claim 19, wherein:
- each of the one or more edge pixels are directly adjacent to eight respective neighboring pixels; and
- wherein the one or more edge pixels are defined such that at least one of the eight respective neighboring pixels has a respective numeric value greater than the intensity threshold ($I_0$) and at least another of the eight respective neighboring pixels N1, to N8, has a respective numeric value less than the intensity threshold ($I_0$).

\* \* \* \* \*